US008404847B2

(12) United States Patent
Koyama

(10) Patent No.: US 8,404,847 B2
(45) Date of Patent: Mar. 26, 2013

(54) METHOD FOR PRODUCING DIAMINE DERIVATIVE

(75) Inventor: Takeo Koyama, Hiratsuka (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 5 days.

(21) Appl. No.: 13/162,922

(22) Filed: Jun. 17, 2011

(65) Prior Publication Data
US 2011/0275821 A1 Nov. 10, 2011

Related U.S. Application Data

(63) Continuation of application No. PCT/JP2009/070874, filed on Dec. 15, 2009.

(30) Foreign Application Priority Data

Dec. 17, 2008 (JP) ................................. 2008-320693

(51) Int. Cl.
A61K 31/44 (2006.01)
C07D 513/02 (2006.01)
(52) U.S. Cl. ....................................... 546/114; 514/301
(58) Field of Classification Search .................. 546/114
See application file for complete search history.

(56) References Cited

U.S. PATENT DOCUMENTS

| 5,055,600 | A | 10/1991 | Wagner |
| 5,149,855 | A | 9/1992 | Sakimae et al. |
| 5,677,469 | A | 10/1997 | van Eikeren et al. |
| 7,192,968 | B2 | 3/2007 | Yoshino et al. |
| 7,342,014 | B2 | 3/2008 | Ohta et al. |
| 7,365,205 | B2 | 4/2008 | Ohta et al. |
| 7,576,135 | B2 | 8/2009 | Ohta et al. |
| 7,674,904 | B2 | 3/2010 | Doshan et al. |
| 2004/0122063 | A1 | 6/2004 | Yoshino et al. |
| 2005/0020645 | A1 | 1/2005 | Ohta et al. |
| 2005/0119486 | A1 | 6/2005 | Ohta et al. |
| 2005/0245565 | A1 | 11/2005 | Ohta et al. |
| 2006/0252837 | A1 | 11/2006 | Ohta et al. |
| 2006/0275357 | A1 | 12/2006 | Oomura et al. |
| 2007/0135476 | A1 | 6/2007 | Nagasawa et al. |
| 2008/0015215 | A1 | 1/2008 | Ohta et al. |
| 2009/0105491 | A1 | 4/2009 | Sato et al. |
| 2009/0192313 | A1 | 7/2009 | Nagasawa et al. |
| 2009/0270446 | A1 | 10/2009 | Ohta et al. |
| 2009/0281074 | A1 | 11/2009 | Ohta et al. |
| 2010/0081685 | A1 | 4/2010 | Kojima et al. |

FOREIGN PATENT DOCUMENTS

| JP | 4-227629 | 8/1992 |
| JP | 11-180899 | 7/1999 |
| JP | 2000-344735 | 12/2000 |
| JP | 2001-151724 | 6/2001 |
| JP | 2008-542287 | 11/2008 |
| WO | WO 01/74774 | 10/2001 |
| WO | WO 03/000657 | 1/2003 |
| WO | WO 03/000680 | 1/2003 |
| WO | WO 03/016302 | 2/2003 |
| WO | WO 2004/058715 | 7/2004 |
| WO | WO 2005/047296 | 5/2005 |
| WO | WO 2007/032498 | 3/2007 |
| WO | WO 2008/043996 | 4/2008 |
| WO | WO 2008/129846 | 10/2008 |
| WO | WO 2008/156159 | 12/2008 |

OTHER PUBLICATIONS

PCT International Preliminary Report on Patentability of Int'l App. No. PCT/JP2010/053905 dated Oct. 18, 2011, 5 pages.
International Search Report of Int'l App. No. PCT/JP2010/053905 dated Apr. 21, 2010, 2 pages.
English Translation of PCT Written Opinion of the International Searching Authority of Int'l App. No. PCT/JP2010/053905 dated May 11, 2010, 4 pages.
PCT International Preliminary Report on Patentability of Int'l App. No. PCT/JP2010/053976 dated Oct. 18, 2011, 5 pages.
International Search Report of Int'l App. No. PCT/JP2010/053976 dated Apr. 13, 2010, 2 pages.
English Translation of PCT Written Opinion of the International Searching Authority of Int'l App. No. PCT/JP2010/053976 dated Apr. 13, 2010, 4 pages.
Patani, et al., "Bioisosterism: A rational approach in drug design", *Chem. Rev.* 1996, 3147-3176.
U.S. Appl. No. 13/231,081, filed Sep. 13, 2011, Koutarou Kawanami.
U.S. Appl. No. 13/228,928, filed Sep. 9, 2011, Takeo Koyama et al.
Dubois, D., et al., "Clinical calorimetry. X. A formula to estimate the approximate surface area if the height and weight be known" *Archives of Internal Medicine*, 17, 863-71 (1916).
Elodi, S., et al., "Optimization of conditions for the catalytic effect of the factor IXa-factor VIII complex: probable role of the complex in the amplification of blood coagulation" *Thrombosis Research*, 15(5-6), 617-29 (1979).
Fujimoto, et al., "Studies on the physical surface area of Japanese: Part 18 calculation formulas in three stages over all age" *Japanese Journal of Hygene*, vol. 23(5): 443-450 (1968)—(Contains an English Abstract).
Furugohri, T., et al., "DU-176b, A potent and orally active factor Xa inhibitor: In vitro and in vivo pharmacological profiles" *Journal of Thrombosis and Haemostasis*, 6(9), 1542-1549 (2008).
Goldberg, Si, et al., "Correlation of configuration and rotatory direction for several 4-substituted cyclohexenes" *Journal of Organic Chemistry*, 31:240-243 (1966).

(Continued)

Primary Examiner — D M Seaman
Assistant Examiner — Heidi Reese
(74) Attorney, Agent, or Firm — Locke Lord LLP

(57) ABSTRACT

The present invention provides a method for producing a compound represented by formula (A), the method comprising the steps of: (a) mixing a compound represented by formula (B) with p-toluenesulfonic acid or p-toluenesulfonic acid monohydrate at less than 1 molar equivalent with respect to the compound represented by formula (B) in a solvent under heating; (b) adding additional p-toluenesulfonic acid or p-toluenesulfonic acid monohydrate to the mixed solution under cooling, wherein the additional p-toluenesulfonic acid or p-toluenesulfonic acid monohydrate is added in such an amount that the total molar equivalent thereof with the p-toluenesulfonic acid or p-toluenesulfonic acid monohydrate of step (a) is 1 molar equivalent or more with respect to the compound represented by formula (B) of step (a); and (c) subsequently allowing the mixed solution to crystallize to obtain the compound represented by formula (A).

12 Claims, 1 Drawing Sheet

OTHER PUBLICATIONS

Hylek, E.M., "Drug evaluation: DU-176b, an oral, direct Factor Xa antagonist." Current Opinion in Investigational Drugs, 8, (9), 778-783 (2007).

Johansson, LC, et al., "Comparison of the Pharmacokinetics and Pharacodynamics of Ximelagatran in young and elderly, healthy Japanese men" *Blood* 100, 3980 (2002).

Mendell, J., et al., "The pharmacokinetics and pharmacodynamics of the direct factor Xa inhibitor, edoxaban co-administered with digoxin: a randomized, open-label, dual treatment sequence, parallel-group study" *Journal of Clinical Pharmacology*, 49(9), 1125 (2009).

Mendell, J., et al., "Thorough QT/QTC study with edoxaban to evaluate effect of therapeutic and supratherapeutic exposure on QTC interval duration in healthy subjects" *Journal of Clinical pharmacology* 49(9), 1122 (2009).

Mould, D., et al., "A population pharmacokinetic pharmacodynamic and logistic regression analysis of lotrafiban in patients" *Clinical Pharmacology and Therapeutics* 69(4), 210-222 (2001).

Mueck, W., et al., "Population pharmacokinetics and pharmacodynamic of rivaroxaban—an oral, direct factor Xa inhibitor—in patients undergoing major orthopaedic surgery" *Clinical Pharmacokinetics*, 47(3), 203-216 (2008).

Nohira, H. "4 Diastereomer Method", Edited by CSJ: The Chemical Society of Japan, kogaku Iseitai no Bunri Kikan Kagaku Sosetsu No. 6, 3rd edition, Japan Scientific Societies Press, pp. 45 to 54, (1999).

Product Information, Clexane® and Clexane® Forte, Clexane® PI MKT, #6178v16, pp. 1-19 (2008).

Ridout, G., et al., "Effect of renal function on edoxaban pharmacokinetics (PK) and on population PK/PK-PD model" *Journal of Clinical Pharmcology* 49(9), 1124 (2009).

Schwartz, HM, et al., "Predicting the Enantiomeric Selectivity of Chymotrypsin. Homologous Series of Ester Substrates" *J. Am. Chem. Soc.*, 100, 5199-5203, (1978).

Sixma JJ, et al., "The ideal anti-thrombotic drug" *Thrombosis research*, 68(6), 507-12 (1992).

Takahashi, H. "3.Warfarin Oto no kojinsa" *Kessen to Junkan*, 14(3), 198-202 (2006) (English Translation Provided).

Tanyeli, C, et al., "Enzyme catalyzed reverse enantiomeric separation of methyl (±)-3-cyclohexene-1-carboxylate" *Tetrahedron: Asymmetry*, 15, 2057-2060, (2004).

Trost, BM, et al., "An Asymmetric Synthesis of (+)-Phyllanthoci" Tetrahedron Lett., 32, 1613-1616, (1991).

Vene, N., et al., "High D-dimer levels predict cardiovascular events in patients with chronic atrial fibrillation during oral anticoagulant therapy" *Thrombosis and Haemostasis*, 90(6), 1163-1172 (2003).

International Preliminary Report on Patentability, issued in PCT/JP2009/070613, mailed Jul. 5, 2011.

International Search Report, issued in PCT/JP2009/070613, mailed Feb. 16, 2010.

Written Opinion of the International Searching Authority, issued in PCT/JP2009/070613, mailed Jul. 5, 2011.

International Preliminary Report on Patentability, issued in PCT/JP2009/070874, mailed Jul. 5, 2011.

International Search Report, issued in PCT/JP2009/070874, mailed Mar. 23, 2010.

Written Opinion of the International Searching Authority, issued in PCT/JP2009/070874, mailed Jul. 5, 2011.

International Preliminary Report on Patentability, issued in PCT/JP2009/071016, mailed Jul. 5, 2011.

International Search Report, issued in PCT/JP2009/071016, mailed Feb. 16, 2010.

Written Opinion of the International Searching Authority, issued in PCT/JP2009/071016, mailed Jul. 5, 2011.

International Preliminary Report on Patentability, issued in PCT/JP2010/050128, mailed Aug. 16, 2011.

International Search Report, issued in PCT/JP2010/050128, mailed Apr. 6, 2010.

Written Opinion of the International Searching Authority, issued in PCT/JP2010/050128, mailed Aug. 16, 2011.

International Preliminary Report on Patentability, issued in PCT/JP2010/057990, mailed Dec. 12, 2011.

International Search Report, issued in PCT/JP2010/057990, mailed Jun. 8, 2010.

Written Opinion of the International Searching Authority, issued in PCT/JP2010/057990, mailed Dec. 12, 2011.

International Preliminary Report on Patentability, issued in PCT/JP2010/060261, mailed Dec. 20, 2011.

International Search Report, issued in PCT/JP2010/060261, mailed Sep. 21, 2010.

Written Opinion of the International Searching Authority, issued in PCT/JP2010/060261, mailed Dec. 20, 2011.

U.S. Appl. No. 13/157,590, filed Jun. 10, 2011, Koji Sato.

U.S. Appl. No. 13/163,287, filed Jun. 17, 2011, Takashi Abiko.

U.S. Appl. No. 13/181,596, filed Jul. 13, 2011, Makoto Ono.

U.S. Appl. No. 13/273,360, filed Oct. 14, 2011, Toshiharu Yoshino.

U.S. Appl. No. 13/328,847, filed Dec. 16, 2011, Makoto Kamada.

Blagden, N., et al. "Crystal engineering of active pharmaceutical ingredients to improve solubility and dissolution rates." *Advanced Drug Delivery Reviews*, 59:603-616 (2007).

Serajuddin, A., "Salt formation to improve drug solubility." *Advanced Drug Delivery Reviews*, 59:617-630 (2007).

Ohta, T., et al. "Preparation of N,N'-bis(heterocyclic acyl)cycloalkanediamine and heterocyclediamine derivatives as inhibitors of activated blood coagulation factor X (factor Xa)", Hcaplus 2003:5928 (2003).

U.S. Appl. No. 13/554,610, filed Jul. 20, 2012, Tetsuya Kimura.

U.S. Appl. No. 13/622,783, filed Sep. 19, 2012, Tetsuya Suzuki.

Supplementary European Search Report mailed Jun. 4, 2012 in EP Application No. 09 83 3467, which corresponds to related U.S. Appl. No. 13/163,287.

Supplementary European Search Report mailed Aug. 30, 2012 in EP Application No. 10769172.0, which corresponds to related U.S. Appl. No. 13/266,967.

Furugohri, T, et al, "Pharmaceutical Characterization, Anti thromboti and Bleeding Effects of DU-176b", Journal of Thrombosis and Haemostasis, 3(supp. 1), Abstract P1110, (2005).

Mohammad, UZ, et al., "Antithrombotic effects of factor Xa inhibition with DU-176b: Phase-I study of an oral, direct factor Xa inhibitor using an ex-vivo flow chamber", Thrombosis and Haemostasis, 98(4):833-888 (2007).

Walker, MB, "Understanding the PT-INR Test", obtained from the internet www.vclotacare.com/ptinr.aspx (retrieved Apr. 24, 2012).

Anonymous, "A phase 2, randomized, parallel group, multi-center, multi-national study for the evaluation of safety and efficacy of two fixed dosages of DU-176b in subjects with non-valvular atrial fibrillation", Clinical Trials.gov NCT00806624 obtained from the internet clinicaltrials.gov/archive/NCT00806624/2008_12_10 (retrieved Apr. 23, 2012).

Kozma, D., "CRC Handbook of Optical Resolutions Via Diastereomeric Salt Formation", CRC Press: Washington, DC, Chapters 4, 5, and 6 (2002).

Murakami, "Asymmetric Transformation of a Raccmic a-(Phthalimidooxy)arylacctic Ester by a Combination of Preferential Crystallization and Simultaneous Racemization" *Chirality* 5141-48 (1993).

Allan, R., "Synthesis of analogs of GABA. VI. Stereoisomers of cis-3-aminocyclohexanecarboxylic acid" *Australian Journal of Chemistry*, 34(10):2231-36 (Abstract only).

Chiappe, et al. "Nucleophilic Displacement Reactions in Ionic Liquids: Substrate and Solvent Effect in the Reaction of $NaN_3$ and KCN with Alkyl Halides and Tosylates," *Journal of Organic Chemistry* 68:6710-15 (2003).

Betti, C., et al. "Reactivity of anionic nucleophiles in ionic liquids and molecular solvents," *Tetrahedron* 64:1689 (2008).

Thomas, M., et al, "Management of Venous Thromboembolism", *Arch Intern Med.*, 163:759-768 (2003).

Turpie, Agg., "Oral, direct factor Xa inhibitors in development for the prevention and treatment of thromboembolic diseases", *Arteriosclerosis, Thrombosis, and Vascular Biology*, 27:1238-1247 (2007).

De Caterina, R, et al. "Anticoagulants in heart disease: current status and perspectives", *European Heart Journal* 28:880-913 (2007).

Dyke, CK., "First experience with direct factor Xa inhibition in patients with stable coronary disease: a pharmacokinetic and pharmacodynamics evaluation", *Circulation.*, 105:2385-2391 (2002).

Iba, T., et al., "Factor Xa-inhibitor (DX-9065a) modulates the leukocyte-endothelial cell interaction in endotoxemic rat", *Shock.*, 17(2):159-162 (2002).

Office of Generic Drugs, "Scoring Configuration of Generic Drug Products", dated Nov. 1, 1995; www.fda.gov/downloads/AboutFDA/CentersOffices/CDER/ManualofPoliciesProcedures/ucm079779.pdf; accessed Sep. 6, 2012; cited in related U.S. Appl. No. 13/163,287.

International Search Report, issued in related International Application No. PCT/JP2011/055955, mailed May 24, 2011.

Written Opinion of the International Searching Authority, issued in related International Application No. PCT/JP2011/055955, mailed May 24, 2011.

METHOD FOR PRODUCING DIAMINE DERIVATIVE

This application is a continuation of International Application No. PCT/JP2009/070874, filed on Dec. 15, 2009, entitled "METHOD FOR PRODUCING DIAMINE DERIVATIVE", which claims the benefit of Japanese Patent Application Number JP 2008-320693, filed on Dec. 17, 2008, all of which are hereby incorporated by reference.

FIELD OF THE INVENTION

The present invention relates to a method for producing a compound that exhibits an inhibitory effect on activated blood coagulation factor X (FXa), and is useful as a preventive and/or therapeutic drug for thrombotic diseases.

BACKGROUND OF THE INVENTION $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonic acid monohydrate represented by the following formula (A) (hereinafter, also referred to as compound A):

[Formula 1]

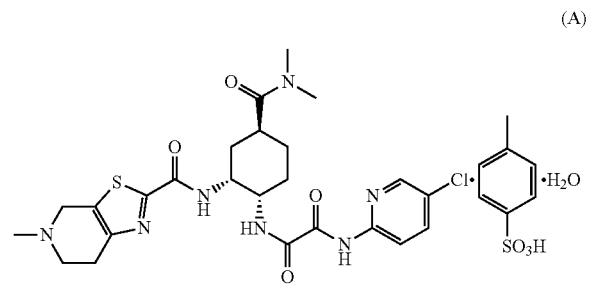

(A)

is known as a compound that exhibits an inhibitory effect on activated blood coagulation factor X (FXa), and is useful as a preventive and/or therapeutic drug for thrombotic diseases (Patent Literature 1 to 8).

For example, a method comprising mixing the free form of compound A represented by the following formula (B) (hereinafter, also referred to as compound B):

[Formula 2]

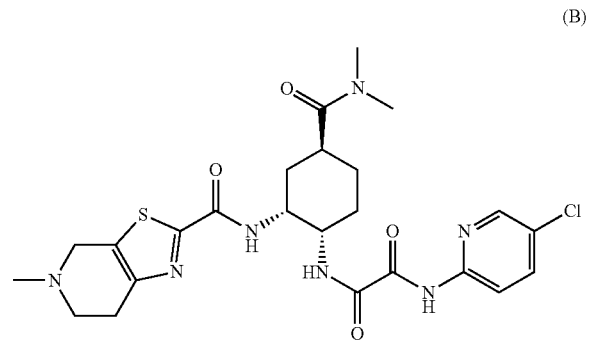

(B)

with p-toluenesulfonic acid or p-toluenesulfonic acid monohydrate, followed by crystallization from aqueous ethanol, is known as a method for obtaining compound A (Patent Literature 1 to 8). These literature documents do not make any mention about adding p-toluenesulfonic acid or p-toluenesulfonic acid monohydrate in a stepwise manner in the step of obtaining compound A from compound B.

CITATION LIST

Patent Literature

Patent Literature 1: International Publication No. WO 03/000657
Patent Literature 2: International Publication No. WO 03/000680
Patent Literature 3: International Publication No. WO 03/016302
Patent Literature 4: International Publication No. WO 04/058715
Patent Literature 5: International Publication No. WO 05/047296
Patent Literature 6: International Publication No. WO 07/032,498
Patent Literature 7: International Publication No. WO 08/129,846
Patent Literature 8: International Publication No. WO 08/156,159

SUMMARY OF INVENTION

Technical Problem

The present inventor has attempted industrial production of compound A, and consequently found that the step of obtaining compound A from compound B results in a great loss of compound A into the mother liquor during the crystallization of compound A from a solvent, and the yield differs depending on each production lot, and differences between the yields of lots are approximately 6% at the maximum. Such loss into the mother liquor or unevenness in yield is not favorable from the viewpoint of efficient production of pharmaceutical drugs. It has thus been demanded to improve these problems and produce compound A at stable high yields.

Solution to Problem

As a result of conducting diligent studies to solve the problems, the present inventor has found that, surprisingly, compound A can be obtained at stable high yields without unevenness, with suppressed decomposition of compound B and reduced loss of compound A into the mother liquor, by an exceedingly convenient approach suitable for industrial production, in which the amount of p-toluenesulfonic acid is reduced when compound B is dissolved in a solvent, and the amount of p-toluenesulfonic acid is increased when compound A is crystallized.

Advantageous Effects of Invention

According to the present invention, compound A can be synthesized from compound B at stable high yields without unevenness by adding p-toluenesulfonic acid or its hydrate in divided portions.

BRIEF DESCRIPTION OF DRAWINGS

FIG. 2 depicts time-dependent (hr; abscissa) change in the amount of compound B (%; ordinate) with the initial (0 hr) amount of compound B defined as 100%.

DETAILED DESCRIPTION

Figure 1:
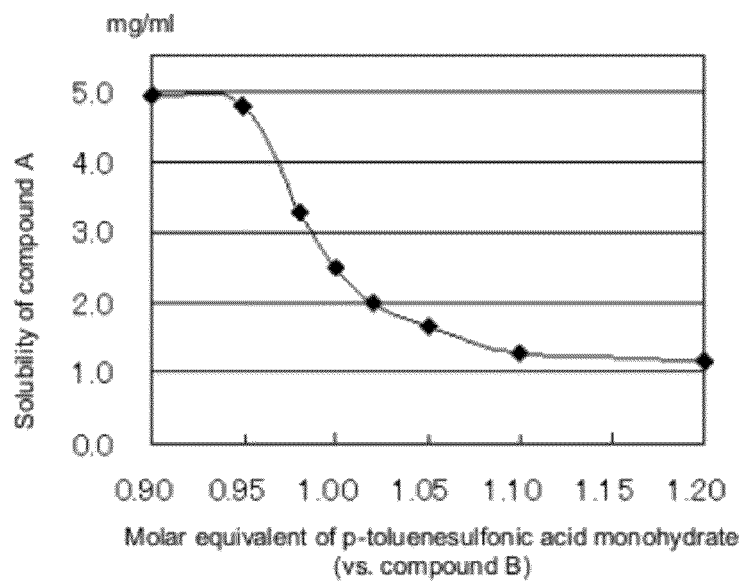
FIG. 1 shows the solubility of compound A obtained by varying the amount of p-toluenesulfonic acid monohydrate under conditions for crystallizing compound A (ethanol having a water content of 10%, 10° C.). The ordinate depicts the solubility (mg/ml) of compound A, and the abscissa depicts the molar equivalent of p-toluenesulfonic acid monohydrate (vs. compound B).

Specifically, the present invention relates to the following:
[1] a method for producing a compound represented by the following formula (A), comprising the steps of:
(a) mixing a compound represented by formula (B):

[Formula 3]

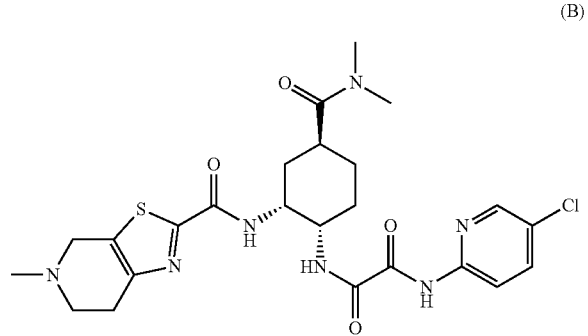 [SMILES: CN1CCc2nc(C(=O)N[C@@H]3C[C@@H](C(=O)N(C)C)CC[C@@H]3NC(=O)C(=O)Nc3ccc(Cl)cn3)sc2C1]

(B)

with p-toluenesulfonic acid or p-toluenesulfonic acid monohydrate at less than 1 molar equivalent with respect to the compound represented by formula (B) in a solvent under heating;
(b) adding additional p-toluenesulfonic acid or p-toluenesulfonic acid monohydrate to the mixed solution under cooling, wherein
the additional p-toluenesulfonic acid or p-toluenesulfonic acid monohydrate is added in such an amount that the total molar equivalent thereof with the p-toluenesulfonic acid or p-toluenesulfonic acid monohydrate of step (a) is 1 molar equivalent or more with respect to the compound represented by formula (B) of step (a); and
(c) subsequently allowing the mixed solution to crystallize to obtain the compound represented by formula (A):

[Formula 4]

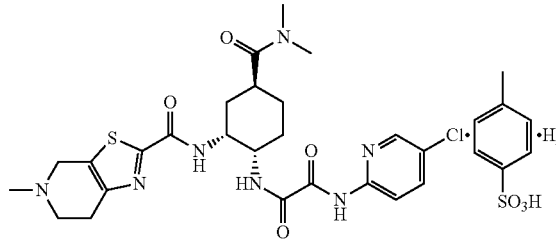

(A)

[2] the method according to [1], wherein the p-toluenesulfonic acid or p-toluenesulfonic acid monohydrate of step (a) is at 0.5 molar equivalent or more and less than 1.0 molar equivalent with respect to the compound represented by formula (B);

[3] the method according to [1] or [2], wherein the p-toluenesulfonic acid or p-toluenesulfonic acid monohydrate of step (a) is at 0.8 molar equivalent or more and less than 1.0 molar equivalent with respect to the compound represented by formula (B);

[4] the method according to any one of [1] to [3], wherein the total molar equivalent of the p-toluenesulfonic acid or p-toluenesulfonic acid monohydrate of the step (a) and the additional p-toluenesulfonic acid or p-toluenesulfonic acid monohydrate added in step (b) is between 1.0 molar equivalent and 3.0 molar equivalents inclusive with respect to the compound represented by formula (B) of step (a);

[5] the method according to any one of [1] to [4], wherein the total molar equivalent of the p-toluenesulfonic acid or p-toluenesulfonic acid monohydrate of step (a) and the additional p-toluenesulfonic acid or p-toluenesulfonic acid monohydrate added in step (b) is between 1.0 molar equivalent and 1.2 molar equivalents inclusive with respect to the compound represented by formula (B) of step (a);

[6] the method according to any one of [1] to [5], wherein the solvent is an alcohol or an aqueous alcohol;

[7] the method according to any one of [1] to [6], wherein the solvent is aqueous ethanol;

[8] the method according to any one of [1] to [7], wherein the aqueous ethanol has a water content of greater than 0% and less than or equal to 50%;

[9] the method according to any one of [1] to [8], wherein p-toluenesulfonic acid monohydrate is used;

[10] the method according to any one of [1] to [9], wherein the amount of the solvent is from 5 times to 30 times (v/w) that of compound B;

[11] the method according to any one of [1] to [10], wherein the heating temperature of step (a) is 60° C. to 80° C.; and

[12] the method according to any one of [1] to [11], wherein the cooling temperature of step (b) is −20° C. to 40° C.

Hereinafter, the method of the present invention will be described in detail.

Scheme 1

[Formula 5]

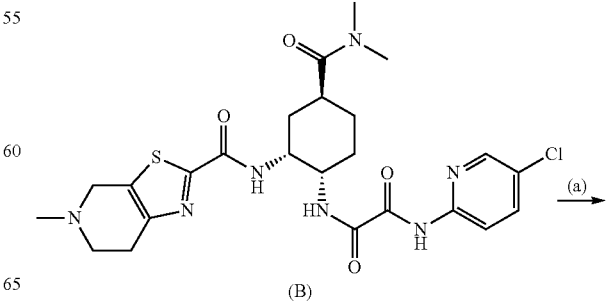

(B)

(a)

-continued

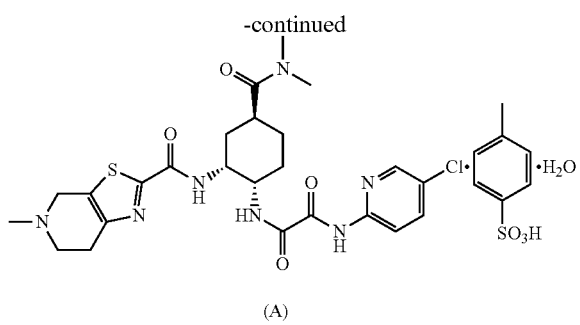

(A)

N¹-(5-chloropyridin-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by formula (B) is the free form of compound A and has been registered as International Nonproprietary Name (INN): edoxaban, (N-(5-chloropyridin-2-yl)-N'-[(1S,2R,4S)-4-(N,N-dimethylcarbamoyl)-2-(5-methyl-4,5,6,7-tetrahydro[1,3]thiazolo[5,4-c]pyridine-2-carboxamido)cyclohexyl]oxamide) in the World Health Organization (WHO).

Step (a) is the step of obtaining compound A from compound B and p-toluenesulfonic acid or p-toluenesulfonic acid monohydrate.

According to conventional methods, although the yield in the step of obtaining compound A from compound B has been relatively favorable, there is still a great loss of compound A into the mother liquor, and yields vary depending on each production lot, and differences between the yields of lots are approximately 6% at the maximum. As a result of conducting diligent studies, the present inventor has found that, in the presence of p-toluenesulfonic acid or p-toluenesulfonic acid monohydrate at an excess molar equivalent with respect to compound B during the mixing of the compound B and the p-toluenesulfonic acid or p-toluenesulfonic acid monohydrate in a solvent under heating, the decomposition of compound B is promoted by the excess. The present inventor has further found that the solubility of compound A is reduced when the amount of p-toluenesulfonic acid or p-toluenesulfonic acid monohydrate is an excess molar equivalent with respect to compound B during the crystallization of compound A under cooling.

Based on these findings, the present inventor has developed a method in which the amount of p-toluenesulfonic acid or p-toluenesulfonic acid monohydrate is allowed to be a smaller molar equivalent with respect to compound B during the mixing of the compound B and the p-toluenesulfonic acid or p-toluenesulfonic acid monohydrate in a solvent under heating, to avoid the decomposition of compound B, and the total molar equivalent of p-toluenesulfonic acid or p-toluenesulfonic acid monohydrate is allowed to be in excess with respect to compound B during the crystallization of compound A by adding additional p-toluenesulfonic acid or p-toluenesulfonic acid monohydrate, to reduce the solubility of compound A and loss of compound A into the mother liquor, thereby obtaining compound A at stable high yields without unevenness between production lots.

One of the advantages of the present invention is to obtain compound A at industrially stable high yields by an exceedingly convenient method in which p-toluenesulfonic acid or p-toluenesulfonic acid monohydrate is added in divided portions.

The present invention relates to a method for producing a compound represented by compound A, comprising mixing compound B with p-toluenesulfonic acid or p-toluenesulfonic acid monohydrate in a solvent under heating, subsequently adding additional p-toluenesulfonic acid or p-toluenesulfonic acid monohydrate under cooling, and then allowing the mixed solution to crystallize, wherein the p-toluenesulfonic acid or p-toluenesulfonic acid monohydrate is at less than 1 molar equivalent with respect to compound B during the mixing under heating, and the additional p-toluenesulfonic acid or p-toluenesulfonic acid monohydrate is added such that the total molar equivalent thereof with the p-toluenesulfonic acid or p-toluenesulfonic acid monohydrate added under heating is 1 molar equivalent or more with respect to the compound B added under heating during the crystallization under cooling.

Figure 2:
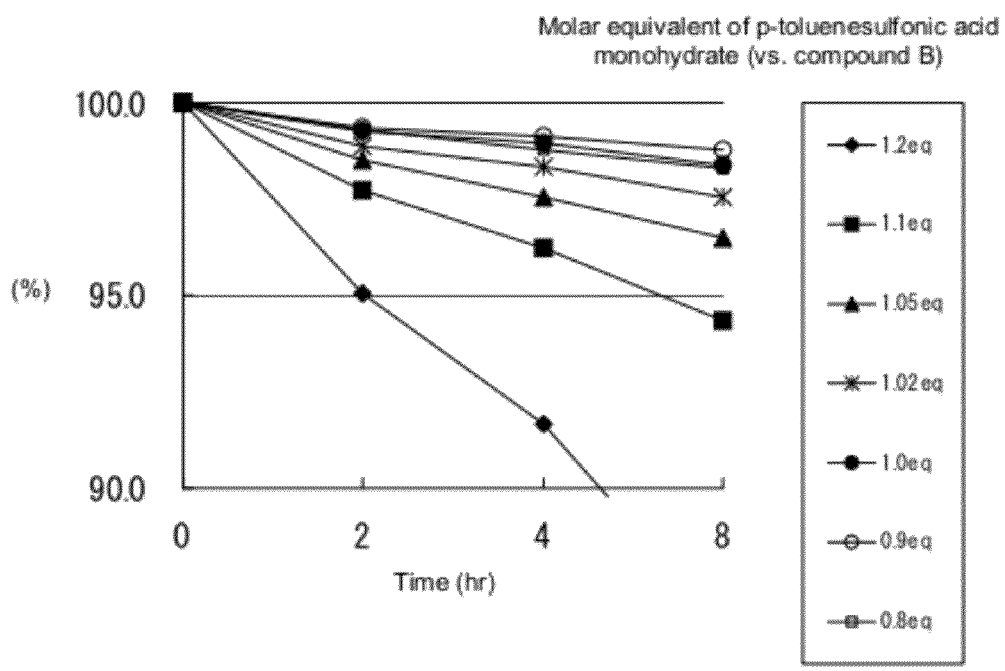
FIG. 2 shows the stability of compound B obtained by varying the amount of p-toluenesulfonic acid monohydrate under conditions for dissolving compound B (ethanol having a water content of 30%, 70° C.).

In the present specification, the "step of mixing a compound represented by formula (B) with p-toluenesulfonic acid or p-toluenesulfonic acid monohydrate at less than 1 molar equivalent with respect to the compound represented by formula (B) in a solvent under heating" as step (a) means mixing the compound B with the p-toluenesulfonic acid or p-toluenesulfonic acid monohydrate at less than 1 molar equivalent with respect to compound B in a solvent under heating. As shown in FIG. 2, the decomposition of compound B is suppressed by allowing the p-toluenesulfonic acid or p-toluenesulfonic acid monohydrate to be at less than 1 molar equivalent with respect to compound B. The "p-toluenesulfonic acid or p-toluenesulfonic acid monohydrate at less than 1 molar equivalent" means that the p-toluenesulfonic acid or p-toluenesulfonic acid monohydrate added in this step is at less than 1 molar equivalent with respect to the compound B added in this step. The "p-toluenesulfonic acid or p-toluenesulfonic acid monohydrate at less than 1 molar equivalent" specifically means that the p-toluenesulfonic acid or p-toluenesulfonic acid monohydrate added in this step is, for example, at 0.5 molar equivalent or more and less than 1.0 molar equivalent with respect to the compound B added in this step, and preferably means that this amount is 0.6 molar equivalent or more and less than 1.0 molar equivalent, 0.7 molar equivalent or more and less than 1.0 molar equivalent, 0.8 molar equivalent or more and less than 1.0 molar equivalent, or 0.95 molar equivalent or more and less than 1.0 molar equivalent, with respect thereto.

The order in which the compound B and the p-toluenesulfonic acid or p-toluenesulfonic acid monohydrate are added to the solvent is not particularly limited. Preferably, compound B is added to the solvent, and then the p-toluenesulfonic acid or p-toluenesulfonic acid monohydrate is added. The p-toluenesulfonic acid or p-toluenesulfonic acid monohydrate may be added in one portion or in divided portions in this step as long as it is added at less than 1 molar equivalent. Preferably, the p-toluenesulfonic acid or p-toluenesulfonic acid monohydrate is added in one portion.

The timing of heating is not particularly limited and may be before, during, or in the latter half of the mixing. Preferably, the heating is performed after compound B and the p-toluenesulfonic acid or p-toluenesulfonic acid monohydrate are added to the solvent. The heating temperature is not particularly limited and is, for example, room temperature to 80° C., preferably 60° to 80° C. The heating time is not particularly limited, and the heating can be performed until compound B is dissolved.

When compound B is mixed with the p-toluenesulfonic acid or p-toluenesulfonic acid monohydrate, the compound B may be in a dissolved or slurry form, and is preferably in a form dissolved by heating.

In the present specification, the "step of adding additional p-toluenesulfonic acid or p-toluenesulfonic acid monohydrate to the mixed solution under cooling" as step (b) means adding the additional p-toluenesulfonic acid or p-toluenesulfonic acid monohydrate to the mixed solution with or after cooling of the mixed solution.

In the present specification, the phrase "the additional p-toluenesulfonic acid or p-toluenesulfonic acid monohydrate is added in such an amount that the total molar equivalent thereof with the p-toluenesulfonic acid or p-toluenesulfonic acid monohydrate of step (a) is 1 molar equivalent or more with respect to the compound represented by formula (B) of step (a)" in step (b) means that the additional p-toluenesulfonic acid or p-toluenesulfonic acid monohydrate is added in such an amount that the total molar equivalent of the p-toluenesulfonic acid or p-toluenesulfonic acid monohydrate of step (a) and the additional p-toluenesulfonic acid or p-toluenesulfonic acid monohydrate added in step (b) is 1 or more with respect to the compound B added in step (a). As shown in FIG. 1, the solubility of compound A can be reduced by allowing the p-toluenesulfonic acid or p-toluenesulfonic acid monohydrate to be at 1 molar equivalent or more with respect to compound B in a crystallization solvent (e.g., 10% aqueous ethanol solvent).

The additional p-toluenesulfonic acid or p-toluenesulfonic acid monohydrate "added in such an amount that the total molar equivalent thereof with the p-toluenesulfonic acid or p-toluenesulfonic acid monohydrate of step (a) is 1 molar equivalent or more with respect to the compound represented by formula (B) of step (a)" specifically refers to additional p-toluenesulfonic acid or p-toluenesulfonic acid monohydrate added in such an amount that the total molar equivalent of the p-toluenesulfonic acid or p-toluenesulfonic acid monohydrate added in steps (a) and (b) is, for example, between 1.0 molar equivalent and 3.0 molar equivalents inclusive, preferably between 1.0 molar equivalent and 2.0 molar equivalents inclusive, more preferably between 1.0 molar equivalent and 1.5 molar equivalents inclusive, even more preferably between 1.0 molar equivalent and 1.2 molar equivalents inclusive, further more preferably between 1.0 molar equivalent and 1.1 molar equivalents inclusive, with respect to the compound represented by formula (B) of step (a).

For example, when p-toluenesulfonic acid monohydrate is added at 0.95 molar equivalent in step (a), p-toluenesulfonic acid monohydrate is added at 0.05 molar equivalent or more (vs. the compound B of step (a)) in step (b) in order to allow the total molar equivalent of the p-toluenesulfonic acid or p-toluenesulfonic acid monohydrate added in steps (a) and (b) (vs. the compound B of step (a)) to be 1 molar equivalent or more.

The additional p-toluenesulfonic acid or p-toluenesulfonic acid monohydrate may be added in one portion or in divided portions as long as the total molar equivalent with respect to the compound B of step (a) is finally 1 molar equivalent or more. Preferably, the additional p-toluenesulfonic acid or p-toluenesulfonic acid monohydrate is added in one portion.

The timing of cooling of the crystallization solvent is not particularly limited. The additional p-toluenesulfonic acid or p-toluenesulfonic acid monohydrate can be added during cooling or after cooling, preferably after cooling. The cooling temperature is not particularly limited and is, for example, −20° C. to 50° C., preferably −20° C. to 40° C.

In the method of the present invention, the number of additions of the p-toluenesulfonic acid or p-toluenesulfonic acid monohydrate in divided portions is not particularly limited as long as it is 2 or more. Preferably, the number of additions is 2.

Examples of the solvent in the method of the present invention include, but are not particularly limited to: water; alcohol solvents such as methanol, ethanol, and isopropyl alcohol; ether solvents such as diethyl ether, dipropyl ether, diisopropyl ether, and tetrahydrofuran; ester solvents such as methyl formate, ethyl formate, ethyl acetate, propyl acetate, butyl acetate, and phenyl acetate; halogenated hydrocarbon solvents such as dichloromethane, chloroform, carbon tetrachloride, dichloroethane, and tetrachloroethane; ketone solvents such as acetone, methyl ethyl ketone, and diethyl ketone; hydrocarbon solvents such as hexane, cyclohexane, benzene, and toluene; nitrogen-containing solvents such as acetonitrile, N,N-dimethylformamide, and N,N-dimethylacetamide; and mixed solvents thereof. The solvent used in the present steps is preferably an alcohol or a mixed solvent of water and an alcohol (also referred to as an aqueous alcohol), more preferably ethanol or a mixed solvent of water and ethanol (also referred to as aqueous ethanol).

When an aqueous alcohol (preferably, aqueous ethanol) is used as the solvent in the method of the present invention, its water content is not particularly limited and is, for example, a content of from higher than 0% to 50%, preferably between 5% and 35% inclusive. When an aqueous alcohol (preferably, aqeuous ethanol) is used as the solvent in the method of the present invention, it is preferred to change the water content between the heating and cooling procedures. For example, it is preferred to use an aqueous alcohol of between 25% and 35% inclusive (e.g., aqueous ethanol of between 25% and 35% inclusive) in the heating procedure and use an aqueous alcohol of between 5% and 25% inclusive (e.g., aqueous ethanol of between 5% and 25% inclusive) in the cooling procedure.

The amount of the solvent in the method of the present invention is not particularly limited and is, for example, 5 times to 50 times (v/w (volume/weight)), preferably 5 times to 30 times (v/w), that of compound B.

The compound A thus obtained exhibits a high inhibitory effect on activated blood coagulation factor X (FXa) and as such, is useful as an anticoagulant agent or a preventive and/or therapeutic agent for thrombus or embolism. Compound A is useful as a pharmaceutical drug for mammals including humans, an activated blood coagulation factor Xa inhibitor, an anticoagulant agent, a preventive and/or therapeutic agent for thrombus or embolism, a preventive and/or therapeutic agent for thrombotic disease, for example, a preventive and/or therapeutic agent for cerebral infarction, cerebral embolism, myocardial infarction, angina pectoris, unstable angina, acute coronary syndrome (ACS), pulmonary infarction, pulmonary embolism, thromboembolism or seizure accompanying nonvalvular atrial fibrillation (NVAF), deep vein thrombosis, disseminated intravascular coagulation syndrome, thrombosis after prosthetic valve/joint replacement, thromboembolism after total hip replacement (THR), thrombosis and reocclusion after revascularization, thrombosis at the time of extracorporeal circulation, blood coagulation at the time of blood collection, Buerger's disease, thromboembolism accompanying systemic inflammatory response syndrome (SIRS), or thromboembolism accompanying multiple organ dysfunction syndrome (MODS), or a bulk pharmaceutical for these preventive and/or therapeutic agents.

A pharmaceutical drug containing compound A as an active ingredient is preferably provided in the form of a pharmaceutical composition containing compound A and one or two or more pharmaceutical additives. The dosage form of the pharmaceutical drug of the present invention is not particularly limited. It can be administered orally or parenterally and is preferably administered orally.

Examples of pharmacologically or pharmaceutically acceptable additives used in the production of the pharmaceutical composition can include, but are not limited to, excipients, disintegrants or disintegration aids, binders, lubricants, coating agents, pigments, diluents, bases, solubilizers or solubilization aids, tonicity agents, pH adjusters, stabilizers, propellants, and adhesives.

Examples of preparations suitable for oral administration can include tablets, powders, granules, capsules, solutions, syrups, elixirs, and oily or aqueous suspensions. Moreover, examples of preparations suitable for parenteral administration can include injections, drops, suppositories, inhalants, and patches.

The dose of the pharmaceutical drug of the present invention is not particularly limited, and can be selected appropriately according to various conditions such as the age, body weight, and conditions of a patient. It is preferred to administer the pharmaceutical drug of the present invention at a dose of 1 mg to 1000 mg, preferably 5 mg to 500 mg, more preferably 5 mg to 300 mg, even more preferably 5 mg to 100 mg of the active ingredient per day in an adult, which is administered in one portion or in several portions, preferably in one portion or in two portions, per day, according to the conditions.

Hereinafter, Examples will be described. However, the present invention is not intended to be limited to them.

EXAMPLES

In the Examples below, p-toluenesulfonic acid monohydrate is also referred to as $TsOH \cdot H_2O$.

Example 1

Synthesis of $N^1$-(5-chloropyridin-2-yl)-$N^2$-((1S,2R,4S)-4-[(dimethylamino)carbonyl]-2-[([(5-methyl-4,5,6,7-tetrahydrothiazolo[5,4-c]pyridin-2-yl)carbonyl]amino]cyclohexyl)ethanediamide (compound B)

Compound B was synthesized according to a method described in Patent Literature 1 to 8.

Example 2

Synthesis of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonic acid monohydrate (compound A)

$TsOH \cdot H_2O$ (49.5 g) was added to a mixed solution of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (150 g), ethanol (735 ml), and water (315 ml), and the mixture was heated to 70° C. The dissolved solution was filtered through a filter, and the filter was washed with 15% aqueous ethanol (300 ml) and ethanol (150 ml). Subsequently, a mixed solution of the filtered mother liquor and the washes was slowly cooled, and $TsOH \cdot H_2O$ (7.8 g) and ethanol (2100 ml) were added thereto. After stirring at 10° C. for 1 hour, crystals were collected by filtration, to obtain 188.9 g of the title compound.

Test Example 1

The solubility of compound A was determined using varying amounts of $TsOH \cdot H_2O$ under conditions for crystallizing compound A (ethanol having a water content of 10%, 10° C.). Specifically, compound A, compound B, and $TsOH \cdot H_2O$ were added in the combinations shown below to 10 ml of ethanol having a water content of 10%. The resulting slurry was stirred at 10° C., and crystals were collected by filtration. Then, the content of the compound A contained in the filtered mother liquor was measured by HPLC (column: Shiseido CAPCELL PAK CN UG120 (4.6×250 mm), column temperature: 40° C., flow rate: 1.0 ml/min., mobile phase: acetonitrile:0.02 M phosphate buffer (pH 7.0)=30:70).

TABLE 1

| Molar equivalent of $TsOH \cdot H_2O$ with respect to compound B*[1] | Compound A (mg) | Compound B (mg) | $TsOH \cdot H_2O$ (mg) |
|---|---|---|---|
| 1.2 | 561 | 0 | 29 |
| 1.1 | 561 | 0 | 14 |
| 1.05 | 561 | 0 | 7 |
| 1.02 | 561 | 0 | 3 |
| 1.0 | 561 | 0 | 0 |
| 0.98 | 550 | 8 | 0 |
| 0.95 | 533 | 21 | 0 |
| 0.90 | 505 | 42 | 0 |

*[1]"Molar equivalent of $TsOH \cdot H_2O$ with respect to compound B" described here refers to the ratio of the sum of the molar number of $TsOH \cdot H_2O$ and the molar number of $TsOH \cdot H_2O$ present as a part of the compound A to the sum of the molar number of the compound B and the molar number of the compound B present as a part of the compound A.

The results are shown in FIG. 1.

It was found that the solubility of compound A is reduced when the amount of $TsOH \cdot H_2O$ is larger than 1.00 molar equivalent of $TsOH \cdot H_2O$ with respect to compound B, and the solubility thereof is increased when the amount of $TsOH \cdot H_2O$ is smaller than this molar equivalent.

Test Example 2

The stability of compound B was determined using varying amounts of $TsOH \cdot H_2O$ under conditions for dissolving compound B in a solvent (ethanol having a water content of 30%, 70° C.). Specifically, 7 ml of ethanol having a water content of 30% and $TsOH \cdot H_2O$ were added in combinations shown below to 1.0 g of compound B, followed by dissolution at 70° C. The content of the compound B was measured at constant time intervals by HPLC (column: Shiseido CAPCELL PAK CN UG120 (4.6×250 mm), column temperature: 40° C., flow rate: 1.0 ml/min., mobile phase: acetonitrile:0.02 M phosphate buffer (pH 7.0)=30:70).

TABLE 2

| Molar equivalent of $TsOH \cdot H_2O$ with respect to compound B | $TsOH \cdot H_2O$ (mg) |
|---|---|
| 1.2 | 416 |
| 1.1 | 382 |
| 1.05 | 364 |
| 1.02 | 354 |
| 1.0 | 347 |
| 0.9 | 312 |
| 0.8 | 278 |

The results are shown in FIG. 2.

It was demonstrated that in the presence of $TsOH \cdot H_2O$ at more than 1.0 molar equivalent (vs. compound B) under conditions for dissolving compound B, the decomposition of compound B (decrease in compound B content) is promoted with the excess, whereas the decomposition is suppressed in the presence thereof at less than 1.0 molar equivalent.

Test Example 3

Based on the results of Test Examples 1 and 2, the present inventor had an idea that the excess of p-toluenesulfonic acid that promotes the decomposition of compound B be avoided for dissolving compound B under high temperatures, and the excess of p-toluenesulfonic acid under low temperatures be created for crystallization to reduce the solubility of compound A, resulting in improvement in the yield of step (a). An attempt was made to perform a p-toluenesulfonic acid division method reflecting this idea.

Specifically, 21 ml of water, 49 ml of ethanol, and 3.30 g of TsOH·H$_2$O (0.95 molar equivalent with respect to compound B) were added to 10.0 g of compound B, followed by dissolution at 70° C. The dissolved solution was filtered through a filter, and the filter was washed with a mixed solution of 3 ml of water and 17 ml of ethanol. Subsequently, a mixed solution of the filtered mother liquor and the washes was slowly cooled, and 521 mg of TsOH·H$_2$O (0.15 molar equivalent with respect to compound B) and 150 ml of ethanol were added thereto. After stirring at 10° C., crystals of compound A were collected by filtration, and its yield was determined. Moreover, two lots of compound B were used to evaluate reproducibility. To prepare a control, 21 ml of water, 49 ml of ethanol, and 3.47 g of TsOH·H$_2$O (1.0 molar equivalent with respect to compound B) were added to 10.0 g of compound B, followed by dissolution at 70° C. The dissolved solution was filtered through a filter, and the filter was washed with a mixed solution of 3 ml of water and 17 ml of ethanol. Subsequently, a mixed solution of the filtered mother liquor and the washes was slowly cooled, and 150 ml of ethanol was added thereto. After stirring at 10° C., crystals of compound A were collected by filtration, and its yield was determined.

A loss into the mother liquor means the compound A remaining in the mother liquor without being deposited as crystals. Loss into mother liquor (%) described in Table 1 was calculated by converting the weight of the compound A remaining in the mother liquor into the weight of the compound B and indicating this weight as a ratio (%) to the weight of the compound B before the start of the reaction.

The results are shown in Table 3.

TABLE 3

| | Molar equivalent of TsOH·H$_2$O*[1] | | | | |
|---|---|---|---|---|---|
| | Molar equivalent of TsOH·H$_2$O added in dissolution step (70° C.) | Molar equivalent of TsOH·H$_2$O added after slow cooling (10° C.) | Total molar equivalent of TsOH·H$_2$O | Yield of compound A (%)*[2] | Loss into mother liquor (%)*[2] |
| 1 | 0.95 | 0.15 | 1.1 | 93.8 | 4.2 |
| 2 | 0.95 | 0.15 | 1.1 | 94.2 | 3.1 |
| 3 | 1.0 | 0 | 1.0 | 90.5 | 6.7 |

*[1] vs. compound B
*[2] vs. compound B

It was demonstrated that compound A can be obtained at high yields with favorable reproducibility by adding TsOH·H$_2$O in divided portions even if different lots of compound B are used.

The invention claimed is:

1. A method for producing a compound represented by the following formula (A), comprising the steps of:
   (a) mixing a compound represented by formula (B):

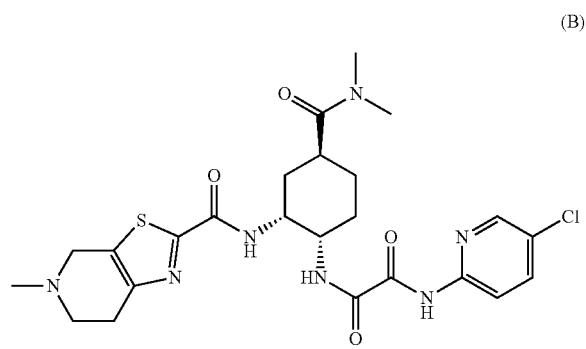

(B)

with p-toluenesulfonic acid or p-toluenesulfonic acid monohydrate at less than 1 molar equivalent with respect to the compound represented by formula (B) in a solvent under heating;
   (b) adding additional p-toluenesulfonic acid or p-toluenesulfonic acid monohydrate to the mixed solution under cooling, wherein
   the additional p-toluenesulfonic acid or p-toluenesulfonic acid monohydrate is added in such an amount that the total molar equivalent thereof with the p-toluenesulfonic acid or p-toluenesulfonic acid monohydrate of step (a) is 1 molar equivalent or more with respect to the compound represented by formula (B) of step (a); and
   (c) subsequently allowing the mixed solution to crystallize to obtain the compound represented by formula (A):

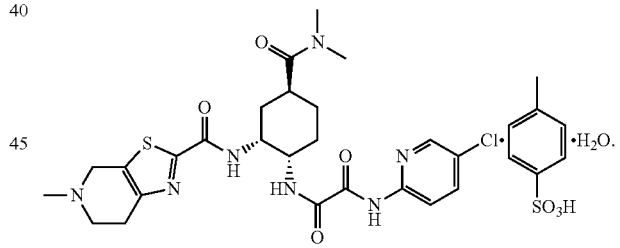

(A)

2. The method according to claim 1, wherein the p-toluenesulfonic acid or p-toluenesulfonic acid monohydrate of step (a) is at 0.5 molar equivalent or more and less than 1.0 molar equivalent with respect to the compound represented by formula (B).

3. The method according to claim 1, wherein the p-toluenesulfonic acid or p-toluenesulfonic acid monohydrate of step (a) is at 0.8 molar equivalent or more and less than 1.0 molar equivalent with respect to the compound represented by formula (B).

4. The method according to claim 1, wherein the total molar equivalent of the p-toluenesulfonic acid or p-toluenesulfonic acid monohydrate of step (a) and the additional p-toluenesulfonic acid or p-toluenesulfonic acid monohydrate added in step (b) is between 1.0 molar equivalent and 3.0 molar equivalents inclusive with respect to the compound represented by formula (B) of step (a).

5. The method according to claim 1, wherein the total molar equivalent of the p-toluenesulfonic acid or p-toluenesulfonic acid monohydrate of step (a) and the additional p-toluenesulfonic acid or p-toluenesulfonic acid monohydrate added in step (b) is between 1.0 molar equivalent and 1.2 molar equivalents inclusive with respect to the compound represented by formula (B) of step (a).

6. The method according to claim 1, wherein the solvent is an alcohol or an aqueous alcohol.

7. The method according to claim 1, wherein the solvent is aqueous ethanol.

8. The method according to claim 1, wherein the aqueous ethanol has a water content of greater than 0% and less than or equal to 50%.

9. The method according to claim 1, wherein p-toluenesulfonic acid monohydrate is used.

10. The method according to claim 1, wherein the amount of the solvent is from 5 times to 30 times (v/w) that of compound B.

11. The method according to claim 1, wherein the heating temperature of step (a) is 60° C. to 80° C.

12. The method according to claim 1, wherein the cooling temperature of step (b) is −20° C. to 40° C.

* * * * *